United States Patent
Klenc et al.

(10) Patent No.: US 10,633,404 B2
(45) Date of Patent: Apr. 28, 2020

(54) METAL TRICARBONYL COMPLEXES COMPRISING SUBSTITUTED IMINODIACTIC ACID LIGANDS AND USES AS RADIOISOTOPE TRACERS

(71) Applicant: Emory University, Atlanta, GA (US)

(72) Inventors: Jeffrey Klenc, Atlanta, GA (US); Malgorzata Lipowska, Atlanta, GA (US); Andrew Taylor, Atlanta, GA (US)

(73) Assignee: Emory University, Atlanta, GA (US)

( * ) Notice: Subject to any disclaimer, the term of this patent is extended or adjusted under 35 U.S.C. 154(b) by 96 days.

(21) Appl. No.: 15/557,453

(22) PCT Filed: Mar. 10, 2016

(86) PCT No.: PCT/US2016/021719
§ 371 (c)(1),
(2) Date: Sep. 11, 2017

(87) PCT Pub. No.: WO2016/145156
PCT Pub. Date: Sep. 15, 2016

(65) Prior Publication Data
US 2018/0057517 A1 Mar. 1, 2018

Related U.S. Application Data (60) Provisional application No. 62/130,953, filed on Mar. 10, 2015.

(51) Int. Cl.
| | |
|---|---|
| *A61K 51/00* | (2006.01) |
| *A61M 36/14* | (2006.01) |
| *C07F 13/00* | (2006.01) |
| *A61K 51/04* | (2006.01) |
| *C07B 59/00* | (2006.01) |
| *A61B 6/00* | (2006.01) |
| *G01N 33/50* | (2006.01) |
| *G01N 33/60* | (2006.01) |

(52) U.S. Cl.
CPC ............ *C07F 13/00* (2013.01); *A61B 6/4057* (2013.01); *A61K 51/0402* (2013.01); *A61K 51/0478* (2013.01); *C07B 59/004* (2013.01); *G01N 33/5088* (2013.01); *G01N 33/60* (2013.01); *G01N 2800/347* (2013.01)

(58) Field of Classification Search
CPC .. C07F 13/00; G01N 33/60; G01N 2800/347; A61K 51/0402; A61K 51/0478
USPC ....................................................... 424/1.89
See application file for complete search history.

(56) References Cited

U.S. PATENT DOCUMENTS

| | | | |
|---|---|---|---|
| 6,926,883 B1 | 8/2005 | Dyszlewski | |
| 9,061,077 B2 | 6/2015 | Lipowska | |
| 2011/0064656 A1* | 3/2011 | Lipowska | A61K 49/0004 424/1.65 |

FOREIGN PATENT DOCUMENTS

| | | |
|---|---|---|
| EP | 0287465 | 1/1993 |
| WO | 2006100562 | 9/2006 |

OTHER PUBLICATIONS

Lipowska et al. J Nulc. Med. 2014, 55, 1206.*
Zhang et al. Curr. Top. Med. Chem. 2007, 7, 1817-1828.*
Wang et al. Nuc. Med. Biol. 2011, 38, 301-312.*
Chopra et al. m-Cyano-p-[18F]fluorohippurate [ [18F]-CNPFH], 2012, In: Molecular Imaging and Contrast Agent Database (MICAD) [Internet]. Bethesda (MD): National Center for Biotechnology Information (US); 2004-2013. Available from: https://www.ncbi.nlm.nih.gov/books/NBK114338/.
Francois et al. A functionalized heterobimetallic 99mTc/Re complex as a potential dual-modality imaging probe: synthesis, photophysical properties, cytotoxicity and cellular imaging investigations, Dalton Trans., 2014, 43, 439.
Klenc et al. Synthesis and evaluation of 99mTc(CO)3(FEDA): a new dual-purpose 99mTc/18F renal imaging agent. J. Nucl. Med., 2015, 56(5) (Suppl. 3):654.
Klenc et al. Structure and properties of fac-[ReI(CO)3(NTA)]2-(NTA3- = trianion of nitrilotriacetic acid) and fac-[ReI(CO)3(L)]n-analogues useful for assessing the excellent renal clearance of the fac-[99mTcI(CO)3(NTA)]2-diagnostic renal agent. Inorg. Chem., 2015, 54(13): 6281-6290.
Lipowska et al. Evaluation of promising monoanionic 99mTc-tricarbonyl complexes with uncharged pendant groups as renal tubular tracers. J. Nucl. Med., 2014, 55 (Suppl 1): 1206.
Lipowska et al. Evaluation of promising monoanionic 99mTc-tricarbonyl complexes with uncharged pendant groups as renal tubular tracers. Society of Nuclear Medicine and Molecular Imaging 61st Annual Meeting, St. Louis, MO, (poster presentation). Jun. 2014.
Lipowska et al. Radiosynthesis of Re(CO)3(18F-FEDA), a structural analog of 99mTc(CO)3(FEDA) and new PET tracer for renal imaging and renal function assessment. J. Nucl. Med. 2016, 57(5), (Suppl. 2), 1066.
Lipowska et al. Re(CO)3([18F]FEDA), a new PET renal tracer: pharmacokinetics and metabolism in rats. J. Nucl. Med. 2017, 58(5), (Suppl. 1), 902.
Lipowska et al.99mTc-tricarbonyl-aminopolycarboxylate complexes with uncharged pendant groups: Radiosynthesis and evaluation as potential renal tubular tracers. Nucl. Med. Biol. 2017, 47:48-55.

(Continued)

*Primary Examiner* — Michael G. Hartley
*Assistant Examiner* — Sean R Donohue
(74) *Attorney, Agent, or Firm* — Emory Patent Group (57) ABSTRACT

This disclosure relates to compositions comprising substituted iminodiacetic acid ligands and metal tricarbonyl complexes containing the ligands and derivatives thereof. In certain embodiments, the metal tricarbonyl complexes are used as radioisotope tracers such as renal tracers. In certain embodiments, the metal complexes comprise $^{99m}$Tc or Re. In certain embodiments, the ligands are substituted with a fluorine, a fluorine-18 ($F^{18}$) radioisotope, or other radionuclide.

5 Claims, 2 Drawing Sheets

(56) References Cited

OTHER PUBLICATIONS

Lipowska et al. Initial evaluation of 99mTc(CO)3(ADA) as a new renal tracer in normal volunteers. J. Nucl. Med. 2018, 59 (Suppl.1): 1587.

Lipowska et al. Re(CO)3([18F]FEDA), a novel 18F PET renal tracer: radiosynthesis and preclinical evaluation. Nucl. Med. Biol. 2018, 58:42-50.

Nigam et al. The Organic Anion Transporter (OAT) Family: A Systems Biology Perspective Physiol Rev. 2015, 95(1): 83-123.

Wester et al. Synthesis and Radiopharmacology of O-(2-[18F]fluoroethyl)-L-Tyrosine for Tumor Imaging, J Nucl. Med. 1999; 40:205-212.

\* cited by examiner

METAL TRICARBONYL COMPLEXES COMPRISING SUBSTITUTED IMINODIACTIC ACID LIGANDS AND USES AS RADIOISOTOPE TRACERS

CROSS-REFERENCE TO RELATED APPLICATIONS

This application is the National Stage of International Application Number PCT/US2016/021719 filed Mar. 10, 2016, which claims priority to U.S. Provisional Application No. 62/130,953 filed Mar. 10, 2015. The entirety of each of these applications is hereby incorporated by reference for all purposes.

STATEMENT REGARDING FEDERAL FUNDING

This invention was made in part with government support under Grant No. R37 DK038842 awarded by the NIH. The government has certain rights in the invention.

BACKGROUND

Radiopharmaceuticals are widely employed in nuclear medicine for imaging and for assessing physiological function and disease. Radioisotope renography is a form of kidney imaging involving radioisotopes used to image the kidney, evaluate suspected renal disease, and monitor renal function. The most common radiolabelled pharmaceutical agent used is $Tc^{99m}$-$MAG_3$ (mercaptoacetyltriglycine). Image quality is dependent on rapid removal of the radiotracer from the circulating plasma by the kidney as the rate of removal provides an important measurement of renal function. Renal plasma flow can be measured indirectly with radioiodinated o-iodohippuran ($^{131}$I-OIH) that is generally accepted as a benchmark.

The $^{99m}$Tc-$MAG_3$ tracer is eliminated via the hepatobiliary tract which is exacerbated in patients with impaired renal function. The clearance of $^{99m}$Tc-mercaptoacetyltriglycine ($^{99m}$Tc-$MAG_3$) is 50-65% when compared to $^{131}$I-OIH making the tracer suboptimal for the estimation of renal plasma flow. Thus, improved renal tracers are need.

Klenc et al. report fac-[ReI(CO)$_3$(NTA)]$^{2-}$ and fac-[ReI (CO)$_3$(L)]$^{n-}$ analogues as useful for assessing the renal clearance. Inorg. Chem., 2015, 54 (13), pp 6281-6290. See also Klenc et al. JNM 2015, 56, (Suppl. 3):654; Lipowska et al. J Nucl Med. 2014; 55 (Suppl. 1):1206, and U.S. Pat. Nos. 9,061,077 and 6,926,883.

References cited herein are not an admission of prior art.

SUMMARY

This disclosure relates to compositions comprising substituted iminodiacetic acid ligands and metal tricarbonyl complexes containing the ligands and derivatives thereof. In certain embodiments, the metal tricarbonyl complexes are used as radioisotope tracers such as renal tracers. In certain embodiments, the metal complexes comprise $^{99m}$Tc and/or Re. In certain embodiments, the ligands are substituted with a fluorine, a fluorine-18 ($F^{18}$) radioisotope, or other radionuclide.

In certain embodiments, a metal tricarbonyl complex comprises N-(2-fluoroethyl) iminodiacetic acid as a ligand, e.g., a metal tricarbonyl complex having the formula Re(CO)$_3$(N-(2-fluoroethyl)iminodiacetate), Re(CO)$_3$ (N-(2-$^{18}$fluoroethyl)iminodiacetate), $^{99m}$Tc(CO)$_3$(N-(2-fluoroethyl)iminodiacetate), mixtures or salts thereof. In certain embodiments, a fluoro is $F^{18}$.

In certain embodiments, the disclosure relates to tracer composition comprising a mixture of Re(CO)$_3$(N-(2-$^{18}$fluoroethyl)iminodiacetate) and $^{99m}$Tc(CO)$^3$(N-(2-fluoroethyl) iminodiacetate).

In certain embodiments, the disclosure relates to kits and pharmaceutical composition comprising ligands or metal tricarbonyl complexes disclosed herein. In certain embodiments, the disclosure relates to kits comprising an amount of a tracer comprising a metal tricarbonyl complex disclosed herein or precursor thereof optionally in a sealed container, wherein the amount of the tracer is suitable for imaging a kidney of subject. In certain embodiments, the ligand is N-(2-fluoroethyl)iminodiacetic acid or N-(2-((tosyl)oxy) ethyl)iminodiacetic acid, or Re(CO)$_3$(N-(2-((tosyl)oxy) ethyl)iminodiacetate. In certain embodiments, the kit further comprise a chelator such as a cryptand.

In certain embodiments, the disclosure relates to the precursor metal tricarbonyl complex Re(CO)$_3$(N-(2-((tosyl) oxy)ethyl)iminodiacetate or derivatives. In certain embodiments, the precursor is N-(2-fluoroethyl)iminodiacetic acid, N-(2-hydroxyethyl)iminodiacetic acid, or N-(2-((tosyl)oxy) ethyl)iminodiacetic acid.

In certain embodiments, the disclosure relates to imaging methods comprising a) administering a pharmaceutical composition comprising a metal tricarbonyl complex disclosed herein containing a radionuclide to a subject; b) scanning the subject for emissions; and c) creating an image indicating a location of the metal tricarbonyl complex containing radionuclide in the body, organ, kidney, blood, or other area of the subject. In certain embodiments, the imaging method comprises single photon emission computed tomography (SPECT) and/or PET imaging

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent. Prior to describing the various embodiments, the following definitions are provided and should be used unless otherwise indicated.

The term "renal scintigraphy" as used herein refers to an imaging system including, but not limited to, a gamma camera able to detect and form an image localizing a source of gamma radiation. In the context of the present disclosure, the imaging system may be for an image corresponding to the form of the labeled organ, and in particular of a kidney underlying skin and other tissues. The imaging system may further comprise computer-based apparatus and software intended to produce an image in a form apparent to the observer, and to analyze the image for information such as, but not only, the intensity of the emitted gamma radiation as well as its locality in the subject body. The term "dose amount" as used herein refers to a bolus dose of a renal tracer, and in particular of the tracer. The dose is preferred to be of an amount that, when delivered to the kidney of an animal or human subject, will have a gamma intensity useful for forming an image of the gamma source by a gamma camera. The dose amount being adjusted according to the size, weight, and shape of the recipient subject and the purpose of the study.

As used herein, "alkyl" means a noncyclic straight chain or branched, unsaturated or saturated hydrocarbon such as those containing from 1 to 10 carbon atoms, typically 1 to 4 otherwise designated $C_{1-4}$alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkoxyalkyl" refers an alkyl group as defined above with the indicated number of carbon atoms attached through an alkyl bridge (i.e., $-CH_2-O-CH_2CH_3$).

A chelator is a molecule that contains multiple multivalent atoms, e.g, divalent, with a lone pair of elections (multidentate). The multivalent atoms are typically N, O, S, and mixtures thereof. Examples of chelators include crown ethers (monocyclic) and cryptands (bi- or polycyclic) which contain polyalkoxy or polyethylene glycol groups. 1,10-Diaza-4,7,13,16,21,24-hexaoxabicyclo[8.8.8]hexacosane is the [2.2.2]cryptand where the numbers [2.2.2] indicate the number of ether oxygen atoms in each of the three bridges between the amine nitrogen caps. Cryptands and crown ethers typically bind cations to form salts. Chelators may be anionic if they contain a quaternary ammonium cation.

A "linking group" refers to any variety of molecular arrangements that can be used to bridge two molecular moieties together. An example formula may be $-R_m-$ wherein R is selected individually and independently at each occurrence as: $-CR_mR_m-$, $-CHR_m-$, $-CH-$, $-C-$, $-CH_2-$, $-C(OH)R_n$, $-C(OH)(OH)-$, $-C(OH)H$, $-C(Hal)R_m-$, $-C(Hal)(Hal)-$, $-C(Hal)H-$, $-C(N_3)R_m-$, $-C(CN)R_n-$, $-C(CN)(CN)-$, $-C(CN)-$, $-C(N_3)(N_3)-$, $-C(N_3)H-$, $-O-$, $-S-$, $-N-$, $-NH-$, $-NR_m-$, $-(C=O)-$, $-(C=NH)-$, $-(C=S)-$, $-(C=CH_2)-$, which may contain single, double, or triple bonds individually and independently between the R groups. If an R is branched with an $R_m$ it may be terminated with a group such as $-CH_3$, $-H$, $-CH=CH_2$, $-CCH$, $-OH$, $-SH$, $-NH_2$, $-N_3$, $-CN$, or -Hal, or two branched Rs may form a cyclic structure. It is contemplated that in certain instances, the total Rs or "m" may be less than 100 or 50 or 25 or 10. Examples of linking groups in include bridging alkyl groups and alkoxyalkyl groups.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $-NR_aR_b$, $-NR_aC(=O)R_b$, $-NR_aC(=O)NR_aNR_b$, $-NR_aC(=O)OR_b$, $-NR_aSO_2R_b$, $-C(=O)R_a$, $-C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

"Subject" refers any animal, preferably a human patient, livestock, or domestic pet.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

Iminodiacetate Metal Tricarbonyl Complexes and Derivatives

The tracer $^{99m}Tc(CO)_3$(2-fluoroethyliminodiacetate) (FEDA), i.e., $^{99m}Tc(CO)_3$ complexed with N-(fluoroethyl) iminodiacetic acid (FEDA), showed a rapid renal excretion in rat studies that was in significant excess of the current clinical standard for the same purpose, $^{99m}Tc$-$MAG_3$. $^{99m}Tc(CO)_3$(FEDA) may prepared with $^{18}F$. The clearance of the $^{99m}Tc$-FEDA analog is comparable to the gold standard, $^{131}I$-OIH. The renal excretion exhibited by $^{99m}Tc(CO)_3$ (FEDA) was unexpected due to the fluoroethyl pendant group being less polar and unable to form hydrogen bonds, as the complexes that were previously evaluated such as $^{99m}Tc(CO)_3$ complexes with N-(2-hydroxyethyl)iminodiacetic acid (HDA) and N-(2-acetamido)iminodiacetic acid (ADA), ($^{99m}Tc(CO)_3$(ADA) and $^{99m}Tc(CO)_3$(HDA)).

Figure 2:
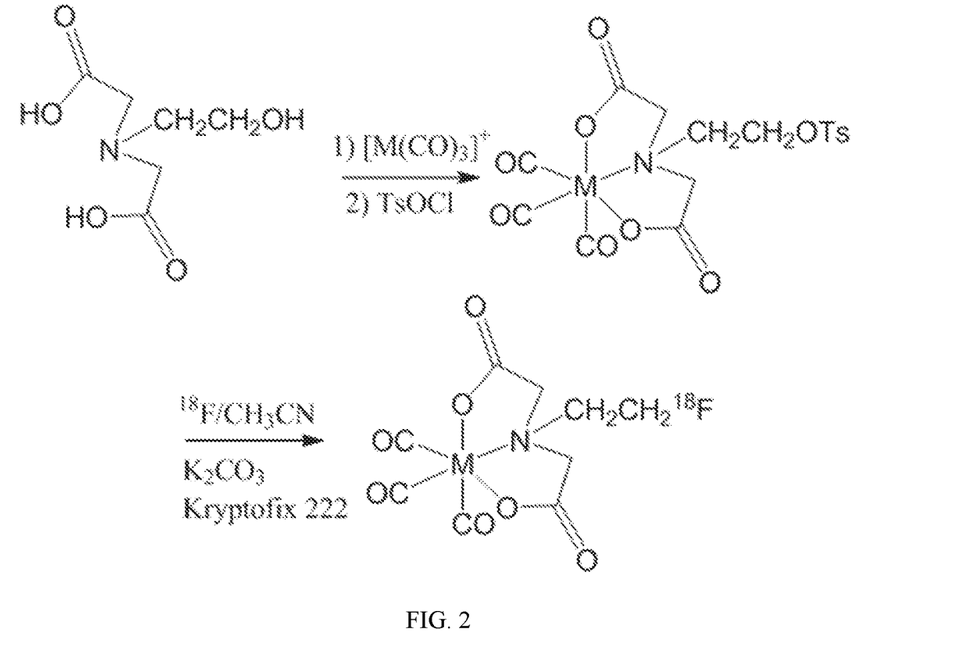
FIG. 2 illustrates the preparation of embodiments of the disclosure, e.g., wherein M is Re or $^{99m}$Tc.
Figure 3:
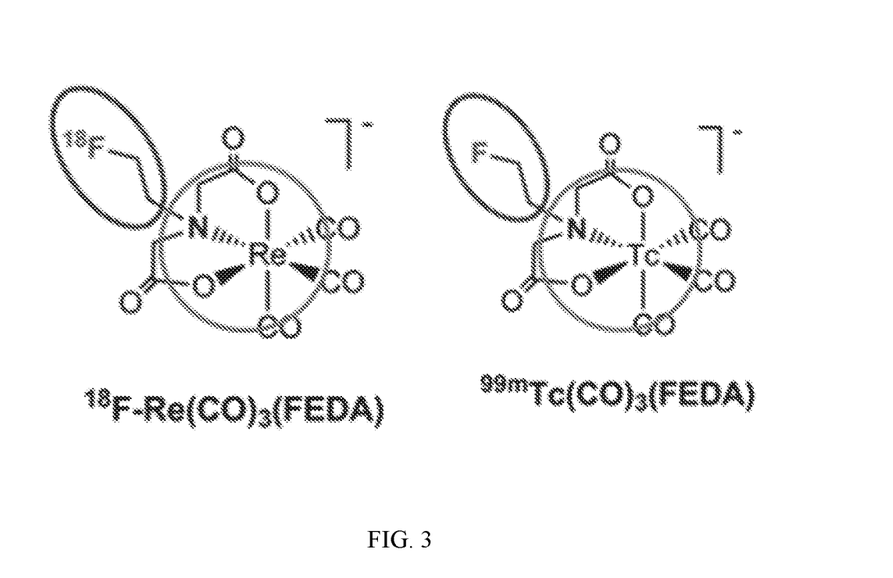
FIG. 3 illustrates embodiments of a renal tracer having a mixture of metal tricarbonyl complexes.

In certain embodiments, the disclosure relates to substituted iminodiacetate metal tricarbonyl complexes disclosed herein, mixtures, and derivatives thereof. In certain embodiments the metal tricarbonyl complexes disclosed herein are substituted with one or more substituents. In certain embodiments, the metal tricarbonyl complexes have the following formula:

or salts thereof wherein

M is $^{99m}Tc$, Re, or other metal capable of octahedral coordination;

X is alkyl, alkoxyalkyl, or other linking group; and

Y is hydroxyl, fluoro, halogen, a leaving group, $F^{18}$, or other radionuclide.

In certain embodiments, metal tricarbonyl complexes of this disclosure comprise N-(fluoroalkyl)iminodiacetate wherein the fluoroalkyl is alkyl terminally substituted with fluoro, e.g., N-(2-fluoroethyl)iminodiacetic acid.

In certain embodiments, metal tricarbonyl complexes of this disclosure have the formula $M(CO)_3$(N-(fluoroalkyl) iminodiacetate), $Re(CO)_3$(N-(fluoroalkyl)iminodiacetate) or $^{99m}Tc(CO)_3$(N-(fluoroalkyl)iminodiacetate).

Generation of Radionuclides

The term "radionuclide" or "radioactive isotope" refers to molecules of enriched isotopes that exhibit radioactive decay (e.g., emitting one or more gamma rays or positrons). Such isotopes are also referred to in the art as radioisotopes. A radionuclide tracer does not include radioactive primordial nuclides, but does include a naturally occurring isotopes that exhibit radioactive decay with an isotope distribution that is enriched, e.g., is several fold greater than natural abundance. In certain embodiments, is contemplated that the radionuclides are limited to those with a half live of less than 1 hour and those with a half-life of more than 1 hour but less than 24 hours. Radioactive isotopes are named herein using various commonly used combinations of the name or symbol of the element and its mass number (e.g., $^{18}F$, F-18, or fluorine-18). Elements that can be used in the compounds of the present disclosure include: F-18; C-11; I-125, I-124, I-131 and I-123; Cl-32, Cl-33, Cl-34; Br-74, Br-75, Br-76, Br-77, Br-78; Re-186, Re-188; Y-90, Y-86; Lu-177 and Sm-153. Typical radioactive isotopes include 1-124, F-18 fluoride, C-11, N-13, and O-15, which have half-lives of 4.2 days, 110 minutes, 20 minutes, 10 minutes and 2 minutes, respectively. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

Methods of preparing radiolabeled ligands are well known in the art. Example of such methods are disclosed in, for example: 1) Jewett, D. M. (1992) A Simple Synthesis of [$^{11}C$]Methyl Triflate Appl. Radiat. Isot. 43, 1383-1385; 2) Crouzel, C. Langstrom, B., Pike, V. W., and Coenen, H. H. (1987) Recommendations for a practical production of [$^{11}C$] methyl iodide Appl. Radiat. Isot. Int. J. Appl. Instrum. Part A 38, 601-603; Dannals, R. F., Ravert, H. T.; 3) Wilson, A. A. (1990) Radiochemistry of Tracers for Neurotransmitter Receptor Studies. In: Quantitative Imaging: Neuroreceptors, Neurotransmitters, and Enzymes. (Edited by Frost), J. J. Wagner Jr., H. N. pp. 19-35, Raven Press, New York; 4) Jewett, D. M., Manger, T. J., and Watkins, G. L. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; 5) Marazano, C., Maziere, M., Berger, G., and Comar, D. (1977) Synthesis of methyl iodide-$^{11}C$ and formaldehyde-$^{11}C$ Appl. Radiat. Isot. 28, 49-52; 6) Watkins, G., Jewett, D., Mulholland, G., Kitbourn, M., and Toorongian, S. (1988) A Captive Solvent Method for Rapid N-[$^{11}C$]Methylation of Secondary Amides Application to the Benzodiazepine, 4'-Chlorodiazepam (RO5-4864) Appl. Radiat. Isot. 39, 441-444; and 7) Wilson, A. A., DaSilva, J. N., and Houle, S. (1996) In vivo evaluation of [$^{11}C$] and [$^{15}F$]-labeled cocaine analogues as potential dopamine transporter ligands for positron emission tomography Nucl. Med. Biol. 23, 141-146.

[$^{18}F$] fluoride is typically produced by irradiation of water (containing $H_2^{18}O$) with protons resulting in the reaction $^{18}O(p,n)^{18}F$. For production efficiency and radiochemical purity, it is desirable to use water that is as highly enriched as possible. The [$^{18}F$] isotope is then separated from water and processed for production of a radiopharmaceutical agent. Typically fluoride recovery is based on ion exchange resins. The recovery is carried out in two steps (extraction and elution): first the anions (not only fluoride) are separated from the enriched [$^{18}O$] water and trapped on a resin and then, said anions, including [$^{18}F$] fluoride, are eluted into a mixture containing water, organic solvents, a base, also called activating agent or phase transfer agent or phase transfer catalyst, such as for example the complex comprising a cryptand, potassium carbonate-Kryptofix 222 ($K_2CO_3$—$K_{222}$), or a tetrabutylammonium salt. Typical labeling method uses low water content solutions. An evaporation step follows the recovery of the [$^{18}$F]fluoride, e.g., azeotropic evaporation of acetonitrile or other low boiling temperature organic solvent.

Alternatively the extraction process is performed by passing the [$^{18}$F] aqueous solution on a solid support as reported in U.S. Pat. No. 8,641,903. This solid support is typically loaded with a trapping agent, e.g., compound comprising a quaternary amine, which is adsorbed on the solid support and allows the [$^{18}$F] activity to be trapped because of its positive charge. The solid support is then flushed with a gas or a neutral solvent to remove or push out most of the residual water. The [$^{18}$F] is at last eluted in an organic solvent or in a mixture of organic solvents and is immediately usable for the labelling of precursor compounds.

The compounds described herein could also be labeled by bromine or iodine radionuclides through traditional labeling procedures such as tributyltin derivatives. (See, for example, Plisson et al, Synthesis and in vivo evaluation of fluorine-18 and iodine-123 labeled 2beta-carbo(2-fluoroethoxy)-3beta-(4'-((Z)-2 iodoethenyl)phenyl)nortropane as a candidate serotonin transporter imaging agent. J Med Chem, 2007, 50(19):4553-60; Plisson et al, Synthesis, radiosynthesis, and biological evaluation of carbon-11 and iodine-123 labeled 2beta-carbomethoxy-3beta-[4'-((Z)-2-haloethenyl)phenyl] tropanes. J Med Chem, 2004, 47(5):1122-35; Li et al, Synthesis of structurally identical fluorine-18 and iodine isotope labeling compounds for comparative imaging. Bioconjug Chem, 2003, 14(2):287-94; Goodman et al., Synthesis and characterization of iodine-123 labeled 2beta-carbomethoxy-3beta-(4'-((Z)-2-iodoethenyl)phenyl)nortropane. J Med Chem, 2003, 46(6):925-35; Maziere et al, $^{76}$Br-beta-CBT, a PET tracer for investigating dopamine neuronal uptake. Nucl Med Biol, 1995, 22(8):993-7).

Kits and Pharmaceutical Compositions

It is appreciated that the stability of metal tricarbonyl complexes disclosed herein containing radionuclides is important to allow for sufficient time, e.g., to complete a renal examination minimizing the possibility of contamination due to formation of disintegration products. Thus, in certain embodiments, metal tricarbonyl complexes containing radionuclides may be prepared immediately prior to conducting a kidney function diagnostic procedure.

Thus in certain embodiments, the disclosure contemplates kits that contain components and the chemical reagents necessary for the preparation of a metal tricarbonyl complex disclosed herein or mixture thereof, immediately prior to use as a radiopharmaceutical. By means of a kit, the labeling reaction of a ligand with a radionuclide may be carried out just prior to use in a clinical laboratory setting. For example, it is typical that one will have access to a molybdenum-technetium generator, from which a desired quantity of $^{99m}$Tc can be obtained as a pertechnetate solution.

F-18 derivatives are typically prepared from precursor compounds by radiohalogenation reactions. Radiohalogenations reactions are typically nucleophilic substitutions. Aliphatic nucleophilic substitutions typically utilize leaving group (usually another halogen or a sulphonic acid derivative such as mesylate, tosylate, or triflate).

In certain embodiments, the disclosure contemplates kits for formation of a radiopharmaceutical metal tricarbonyl complex suitable for renal examination that comprises a precursor metal tricarbonyl complex, e.g., $^{99m}$Tc(CO)$_3$(H$_2$O)$_3$ salts and a ligand having a structure according to the formula:

or salts thereof wherein

X is alkyl, alkoxyalkyl, or other linking group; and

Y is hydroxyl, halogen, a leaving group, fluoro, F$^{18}$, or other radionuclide.

In certain embodiments, the kit further optionally comprises a metal tricarbonyl complex, a reducing agent, a stabilizing agent and/or a chelating agent, as well as instructions for use of the reagents in the kit.

In certain embodiments, the ligand is N-(LGalkyl)iminodiacetic acid wherein the LGalkyl is alkyl terminally substituted with a halogen, fluroro, hydroxyl, leaving group, or salt thereof.

In certain embodiments, the leaving group is Cl, Br, I, a sulfonate, tosylate, mesylate, trifluoromethanesulfonate, or sulfurate.

A $^{99m}$Tc metal tricarbonyl complex may be prepared from a kit by interacting under reducing conditions the reactants of the kit, i.e., a ligand and a freshly prepared. $^{99m}$Tc solution eluted from a molybdenum-technetium generator just prior to use. The $^{99m}$Tc may be present in the form of a salt or as technetium bound to a relatively weak chelator, in which case the desired $^{99m}$Tc chelate is formed by ligand exchange. Examples of relatively weak chelating agents known to be particularly suitable to easily obtain a desired ligand exchange are, for example, carboxylic acids such as citric acid, tartaric acid, ascorbic acid, glucoheptonic acid, and derivatives thereof, although polycarboxylic acids, hydroxycarboxylic acids and phosphorus compounds can also be used.

Suitable reducing conditions to keep the $^{99m}$Tc pertechnetate reduced can be provided by, for example, dithionite, formamidine sulfinic acid or metallic reducing agents such as Fe(II), Cu(I), Ti(III) or Sb(III) and, preferably, Sn(II).

The reactants of the kit may be present in liquid form, for example, as a saline or buffer solution. However, it is preferred that the reactants be in a dry form, e.g., a lyophilized condition. The reactants may be stabilized by the presence of a suitable stabilizing agent such as ascorbic acid, gentisic acid, sugar, e.g., glucose, lactose, mannitol, inositol, and the like.

In certain embodiments, the disclosure also contemplates kits comprising an amount of a tracer comprising a metal tricarbonyl complex disclosed herein, or precursor, or mixtures thereof optionally in a sealed container, wherein the amount of the tracer is suitable for imaging a kidney of subject.

In certain embodiments, the kit further comprises a cryptand or other anionic chelator.

In certain embodiments, the kits comprise metal tricarbonyl complexes or mixtures having the following formula:

or salts thereof wherein

M is $^{99m}$Tc, Re, or other metal capable of octahedral coordination;

X is alkyl, alkoxyalkyl, or other linking group; and

Y is hydroxyl, halogen, I, Br, or a leaving group.

In certain embodiment, the kit further comprises a reagent for generating a leaving group, e.g., Y is hydroxyl and the reagent is capable of reacting with the hydroxyl to form a leaving group such as a tosylate or mesylate group.

In certain embodiment, the kit further comprises a precursor compound of the formula M(CO)$_3$(N-(LGalkyl)iminodiacetate), Re(CO)$_3$(N-(LGalkyl)iminodiacetate) or $^{99m}$Tc(CO)$_3$(N-(LGalkyl)iminodiacetate) wherein LGalkyl is an alkyl terminal substituted with a leaving group or salt thereof.

It is contemplated that precursor metal tricarbonyl complexes are labeled with radionuclides using methods reported herein to provide the tracers. These tracers may be prepared at the location of the subject near the time the subject is exposed to an imaging device. Thus, in certain embodiments, the disclosure contemplates kits comprising metal tricarbonyl complexes disclosed herein or precursors (e.g., metal tricarbonyl complexes disclosed herein that react with recently generated $^{18}$F), e.g., metal tricarbonyl complexes disclosed herein comprising alkyl or alkoxy groups that are terminally substituted with tosylate and mesylate groups.

In certain embodiments, the disclosure contemplates a kit comprising metal tricarbonyl complexes disclosed herein or precursors comprising alkyl or alkoxy groups terminally substituted with halogen, hydroxyl, thiol, —O-p-toluenesulfonyl, —O-p-bromobenzenesulfonyl, —O-(2- or 4)-nitrobenzene sulfonyl, —O-methanesulfonyl, —O-trifluoromethanesulfonyl, —O-5(dimethyl amino)naphthalene-1-sulfonyl, —S-p-toluenesulfonyl, —S-p-bromobenzenesulfonyl, —S-(2- or 4)-nitrobenzene sulfonyl, —S-methanesulfonyl, —S-trifluoromethanesulfonyl, —S-5 (dimethylamino)naphthalene-1-sulfonyl. In certain embodiments, the kit may further comprise a metal tricarbonyl complex disclosed herein having a terminal hydroxy or thiol and an activating agent such as p-toluenesulfonyl chloride, p-bromobenzenesulfonyl chloride, (2- or 4)-nitrobenzene sulfonyl chloride, methanesulfonyl chloride, trifluoromethanesulfonyl chloride, 5(dimethylamino)naphthalene-1-sulfonyl chloride, dicyclohexylcarbodiimide, bromo-tripyrrolidino-phosphonium hexafluorophosphate, bromotris (dimethylamino) phosphonium hexafluorophosphate, 2-(6-Chloro-1H-benzotriazol-1-yl)-N,N,N',N'-tetramethyl aminium hexafluorophosphate, N-[(5-Chloro-1H-benzotriazol-1-yl)-dimethylamino-morpholino]-uronium hexafluorophosphate N-oxide, tetramethylfluoro formamidinium hexa-fluorophosphate, 1-[1-(Cyano-2-ethoxy-2-oxoethylidene-aminooxy)-dimethylamino-morpholino]-uronium hexafluorophosphate, 2-(1-oxy-pyridin-2-yl)-1,1,3,3-tetramethyl-isothiouronium tetrafluoroborate].

In certain embodiments, the kit comprise a solid support comprising $^{18}$F salts.

In some embodiments, the solid support is selected from the group of solid phase extraction resins or liquid chromatography resins, e.g., silica (oxide) based or non-silica (metal oxide or polymers) based particles optionally functionalized (e.g., by organosilanization) with alkyl chains for example C4, C8, C18, C18, C30 or other functional groups, e.g., polar groups (amide, carbamate, sulfamide, and ureas) embedded within alkyl chains or branched alkyl groups or polymeric packings. Polymeric column packing refers to particles made by the process of reacting silica surface silanol groups with halogenated di or trifunctional silanes.

In some embodiments, the solid support is selected from the group consisting of solid phase extraction resins and liquid chromatography resins resulting from the copolymerization of divinylbenzene and/or styrene, or by the copolymerization with vinylpyrrolidone, vinylacetate, (methacryloyloxymethyl)naphtalene, 4,4'-bis(maleimido) diphenylmethane, p,p'-dihydroxydiphenylmethane diglycidylmethacrylic ester, p,p'-dihydroxydiphenylpropane diglycidylmethacrylic ester, 2-hydroxyethylmethacrylate (HEMA), 2,2-dimethylaminoethylmethacrylate (DMAEMA), ethylenedimethacrylate glycidylmethacrylate, N-vinylcarbazole, acrylonitrile, vinylpyridine, N-methyl-N-vinylacetamide, aminostyrene, methylacrylate, ethylacrylate, methylmethacrylate, N-vinylcaprolactam, N-methyl-N-vinylacetamide.

In some embodiments, the solid support comprises or is functionalized with or preconditioned with quaternary ammonium salts, e.g., tetraethylammonium carbonate, tetrabutylammonium carbonate or potassium carbonate cryptands such as 1,4,10-Trioxa-7,13-diaza-cyclopentadecane, 4,7,13,16,21,24-Hexaoxa-1,10-diazabicyclo[8.8.8] hexacosane, 4,7,13,16,21-Pentaoxa-1,10-diazabicyclo [8.8.5]tricosane, 4,7,13,18-Tetraoxa-1,10-diazabicyclo [8.5.5]eicosane, 5,6-Benzo-4,7,13,16,21,24-hexaoxa-1,10-diazabicyclo[8.8.8]hexacos-5-ene; the group of glymes including crown ethers such as for example 4'-Aminobenzo-15-crown-5,4'-Aminobenzo-15-crown-5,4'-Aminobenzo-15-crown-5 hydrochloride, 4'-Aminobenzo-18-crown-6,4'-Aminodibenzo-18-crown-6, 2-Aminomethyl-15-crown-5,2-Aminomethyl-15-crown-5,2-Aminomethyl-18-crown-6,4'-Amino-5'-nitrobenzo-15-crown-5,4'-Amino-5'-nitrobenzo-15-crown-5,1-Aza-12-crown-4,1-Aza-15-crown-5,1-Aza-15-crown-5,1-Aza-18-crown-6, 1-Aza-18-crown-6, Benzo-12-crown-4,5,6-Benzo-4,7,13,16,21,24-hexaoxa-1,10-diazabicyclo[8.8.8]hexacos-5-ene, 1-Benzyl-1-aza-12-crown-4, Bis[(benzo-15-crown-5)-15-ylmethyl]pimelate, 4'-Bromobenzo-15-crown-5, 4-tert-Butylbenzo-15-crown-5, 4-tert-Butylcyclohexano-15-crown-5,4'-Carboxybenzo-15-crown-5, polyethylene glycol s (PEG), polyethylene oxides (PEO); the group of calixarenes such as for example 4-tert-Butylcalix[4]arene, 4-tert-Butylcalix[4]arene, 4-tert-Butylcalix[4]arene, 4-tert-Butylcalix[5]arene, 4-tert-Butylcalix[6] arene, 4-tert-Butylcalix[6]arene, 4-tert-Butylcalix[6]arene, 4-tert-Butylcalix[8]arene, 4-tert-Butylcalix[8]arene, 4-tert-Butylcalix[4]arene-tetraacetic acid tetraethyl ester, 4-tert-Butylcalix[4]arenetetraacetic acid tetraethyl ester, 4-tert-Butylcalix[4]arene-tetraacetic acid triethyl ester, Calix[4] arene, Calix[6]arene, Calix[8]arene, 4-(Chloromethyl)calix [4]arene, 4-Isopropylcalix[4]arene, C-Methylcalix[4] resorcinarene, C-Methylcalix[4]resorcinarene, meso-Octamethylcalix(4)pyrrole, 4-Sulfocalix[4]arene, 4-Sulfocalix[4]arene sodium salt, C-Undecylcalix[4]resorcinarene monohydrate, C-Undecylcalix[4]resorcinarene monohydrate, the group of cyclodextrines such as α-Cyclodextrin, β-Cyclodextrin, γ-Cyclodextrin, (2,6-Di-O-)ethyl-β-cyclodextrin, 6-O-α-D-Glucosyl-β-cyclodextrin, Heptakis(6-O-t-butyldimethyl silyl-2,3-di-O-acetyl)-β-cyclodextrin, Heptakis(2,6-di-O-methyl)-β-cyclodextrin, Heptakis(2,3,6-tri-O-acetyl)-β-cyclodextrin, Heptakis(2,3,6-tri-O-benzoyl)-β-cyclodextrin, Hexakis (6-O-tertbutyl-dimethyl silyl)-α-cyclodextrin, Hexakis (2,3,6-tri-O-acetyl)-α-cyclodextrin, Hexakis (2,3,6-tri-O-methyl)-α-cyclodextrin, (2-Hydroxyethyl)-β-cyclodextrin, 6-O-α-Maltosyl-β-cyclodextrin hydrate, Methyl-β-cyclodextrin, 6-Monodeoxy-6-monoamino-β-cyclodextrin, Octakis (6-O-t-butyldimethylsilyl)-γ-cyclodextrin, Sulfopropyl-β-cyclodextrin, Triacetyl-α-cyclodextrin, Triacetyl-β-cyclodextrin; and the group of EDTA and derivatives such as for example Ethylenediamine-N,N'-diacetic acid, 2-Bis(2-aminophenoxy)ethane-N,N,N',N'-tetraacetic acid, trans-1,2-Diaminocyclohexane-N,N,N',N'-tetraacetic acid monohydrate, trans-1,2-Diaminocyclohexane-N,N,N',N'-tetraacetic acid monohydrate, 1,3-Diamino-2-hydroxypropane-N,N,N',N'-tetraacetic acid, 1,2-Diaminopropane-N,N,N',N'-tetraacetic acid, 1,3-Diaminopropane-N,N,N',N'-tetraacetic acid, 1,3-Diamino-2-propanol-N,N,N',N'-tetraacetic acid, Diethylenetriamine-pentaacetic acid calcium trisodium salt hydrate, N-(2-Hydroxyethyl)ethylenediaminetriacetic acid trisodium salt hydrate, N-(2-Hydroxyethyl)ethylenediamine-N,N',N'-triacetic acid.

Another aspect of the present disclosure provides kits comprising: an amount of a ligand or metal tricarbonyl complex disclosed herein in a sealed container, wherein the amount is suitable for imaging a kidney of an animal or human subject, and instructions for the use thereof in imaging said kidney and optionally for determining renal function in the animal or human subject.

In certain embodiments, the instructions comprise the steps of: administering to an animal or human subject an amount of a renal tracer, where the renal tracer comprises a metal tricarbonyl complex disclosed herein or mixtures; detecting the tracer in the kidney of the animal or human subject with a gamma camera; and obtaining at least one image of the kidney of the animal or human subject, wherein the image is obtained as a data output from a gamma camera. In another embodiment of this aspect of the disclosure, the instructions comprise steps for the use of the tracer in measuring renal function, the instructions comprising the steps of: administering to an animal or human subject an amount of a renal tracer; obtaining at least one image of a kidney of the animal or human subject, wherein the image is obtained as a data output from a gamma camera; and analyzing the data output from the gamma camera, wherein the data analysis provides a measurement of the effective renal plasma flow of the animal or human subject.

In certain embodiments, the instructions for the use of the tracer in measuring renal function comprise the steps of: administering to an animal or human subject an amount of a renal tracer or mixtures; isolating a plurality of biological samples from the animal or human subject after administering the renal tracer; quantitatively measuring the amount of the renal tracer in the isolated biological samples; and determining the effective renal plasma flow of the animal or human subject.

Pharmaceutical compositions for use in the present disclosure typically comprise an effective amount of a metal tricarbonyl complex or mixtures and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

In certain embodiments, the disclosure relates to pharmaceutical composition comprising a metal tricarbonyl complex disclosed herein or mixture thereof. The radioactive diagnostic composition of the invention may be formulated in any appropriate preparation form such as powder, lyophilized powder or solution. Further, it may comprise, in addition to said essential components, any auxiliary agent such as a pH regulating agent (e.g. acid, base), an isotonic agent (e.g. sodium chloride), a preservative (e.g. benzyl alcohol) or the like.

In certain embodiments, the disclosure contemplates pharmaceutical compositions comprising a pharmaceutically acceptable excipient and a compound disclosed herein. In certain embodiments, the pharmaceutical composition is in the form of a tablet, capsule, pill, aerosol, or aqueous buffer, such as a saline or phosphate buffer.

The pharmaceutical composition may contain a water-soluble stabilizer, water-soluble reducing agent such as chloride, stannous fluoride, stannous sulfate, stannous nitrate, stannous acetate, stannous citrate, stannous tartrate, ascorbic acid or erythrobic acid, or any pharmaceutically acceptable salt or ester thereof.

Imaging Methods

Instruments for detecting and monitoring by radionuclide imaging the location of a tracer in the body of a subject include positron emission tomography (PET) and single photon emission computed tomography (SPECT) scanners. These may be combined with other methods such as computerized tomography (CT) scans and MM. A CT scan combines a series of X-ray images taken from different angles and uses computer processing to create cross-sectional images, or slices, of the bones, blood vessels and soft tissues inside your body. These scans or associated data can be used to create computerized images that take place in tissue or the blood stream. A scanner records data that a computer constructs into two- or three-dimensional images. In a typical method, radioactive drug is injected into the subject, e.g., a vein, and a scanner is used to make detailed images of areas inside the body where the radioactive material is taken up by the cells, tissue, fluids, or organs.

Single photon emission computed tomography (SPECT) is a nuclear medicine imaging technique using gamma rays. It may be used with any gamma-emitting isotope, including Tc-99m ($^{99m}Tc$). In the use of technetium-99m, the radioisotope is administered to the patient and the escaping gamma rays are incident upon a moving gamma camera which computes and processes the image. To acquire SPECT images, the gamma camera is typically rotated around the patient. Projections are acquired at defined points during the rotation, typically every three to six degrees. In most cases, a full 360° rotation is used to obtain an optimal reconstruction. SPECT is widely used to obtain clinically significant information about analog binding, localization and clearance rates.

Positron Emission Tomography (PET) involves detection of pairs of gamma rays emitted indirectly by a positron-emitting radionuclide (tracer), which is introduced into the body on a biologically active molecule. Images of tracer concentration in the body are then reconstructed by computer analysis. Two or three-dimensional images of tracer concentration within the area are then constructed by computer analysis. A radioactive tracer is administered to a subject e.g., into blood circulation. Typically there is a waiting period while tracer becomes concentrated in areas of interest; then the subject is placed in the imaging scanner. As the radionuclide undergoes positron emission decay, it emits a positron, an antiparticle of the electron with opposite charge, until it decelerates to a point where it can interact with an electron, producing a pair of (gamma) photons moving in approximately opposite directions. These are detected in the scanning device. The technique typically utilizes simultaneous or coincident detection of the pair of photons moving in approximately opposite direction (the scanner typically has a built-in slight direction-error tolerance). Photons that do not arrive in pairs (i.e. within a timing-window) are typically ignored. One typically localizes the source of the photons along a straight line of coincidence (also called the line of response, or LOR). This data is used to generate an image.

The term "radionuclide" or "radioactive isotope" refers to molecules of enriched isotopes that exhibit radioactive decay (e.g., emitting positrons). Such isotopes are also referred to in the art as radioisotopes. A radionuclide tracer does not include radioactive primordial nuclides, but does include a naturally occurring isotopes that exhibit radioactive decay with an isotope distribution that is enriched, e.g., is several fold greater than natural abundance. In certain embodiments, is contemplated that the radionuclides are limited to those with a half live of less than 1 hour and those with a half-life of more than 1 hour but less than 24 hours. Radioactive isotopes are named herein using various commonly used combinations of the name or symbol of the element and its mass number (e.g., $^{18}$F, F-18, fluorine-18). Elements that can be used in the compounds of the present disclosure include: F-18; C-11; I-125, I-124, I-131 and I-123; Cl-32, Cl-33, Cl-34; Br-74, Br-75, Br-76, Br-77, Br-78; Re-186, Re-188; Y-90, Y-86; Lu-177 and Sm-153. Typical radioactive isotopes include I-124, F-18 fluoride, C-11, N-13, and O-15, which have half-lives of 4.2 days, 110 minutes, 20 minutes, 10 minutes and 2 minutes, respectively. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

Methods of preparing radiolabeled ligands are well known in the art. Example of such methods are disclosed in, for example: 1) Jewett, D. M. (1992) A Simple Synthesis of [$^{11}$C]Methyl Triflate Appl. Radiat. Isot. 43, 1383-1385; 2) Crouzel, C. Langstrom, B., Pike, V. W., and Coenen, H. H. (1987) Recommendations for a practical production of [$^{11}$C] methyl iodide Appl. Radiat. Isot. Int. J. Appl. Instrum. Part A 38, 601-603; Dannals, R. F., Ravert, H. T.; 3) Wilson, A. A. (1990) Radiochemistry of Tracers for Neurotransmitter Receptor Studies. In: Quantitative Imaging: Neuroreceptors, Neurotransmitters, and Enzymes. (Edited by Frost), J. J. Wagner Jr., H. N. pp. 19-35, Raven Press, New York; 4) Jewett, D. M., Manger, T. J., and Watkins, G. L. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; 5) Marazano, C., Maziere, M., Berger, G., and Comar, D. (1977) Synthesis of methyl iodide-$^{11}$C and formaldehyde-$^{11}$C Appl. Radiat. Isot. 28, 49-52; 6) Watkins, G., Jewett, D., Mulholland, G., Kitbourn, M., and Toorongian, S. (1988) A Captive Solvent Method for Rapid N-[$^{11}$C]Methylation of Secondary Amides Application to the Benzodiazepine, 4'-Chlorodiazepam (R05-4864) Appl. Radiat. Isot. 39, 441-444; and 7) Wilson, A. A., DaSilva, J. N., and Houle, S. (1996) In vivo evaluation of [$^{11}$C] and [$^{15}$F]-labeled cocaine analogues as potential dopamine transporter ligands for positron emission tomography Nucl. Med. Biol. 23, 141-146.

It is also contemplated that, besides images over the renal area, static images may also be taken of the pre-injection dose syringe, post-imaging empty dose syringe, the pre-voided bladder, the post-void-bladder, the post-void kidneys, and the injection site. The syringe images are necessary for calculation of renal clearance by the camera-based method. Bladder images are necessary in order to obtain urine flow rate and residual urine volume. The post-void kidney image is a visual indicator of the emptying of urine from the renal collecting systems (since the patient will usually have gotten up from the scan table in order to void). This image also provides kidney counts, from whole kidney regions of interest, which allow calculation of important ratios relevant to the excretory function of the kidneys. The injection site image is a quality control element for the radiopharmaceutical injection, since a significant quantity of the dose outside the vein will invalidate the study.

The baseline study may be analyzed quantitatively and the results reviewed by a physician. If the patient was referred for evaluation of possible obstruction, adequate clearance of the radiopharmaceutical should be seen and, if it is not, an intravenous dose of furosemide, a diuretic, can be administered. An additional dynamic image set is then acquired. In certain embodiments or the present disclosure, therefore provides methods of imaging a kidney in an animal or human subject, the method comprising: (a) administering to an animal or human subject an amount of a renal tracer, where the renal tracer comprises a metal tricarbonyl complex disclosed herein in the kidney of the animal or human subject with a gamma camera; and (c) obtaining at least one image of the kidney of the animal or human subject, where the image is obtained as a data output from a gamma camera.

In certain embodiments the present disclosure encompasses methods of measuring renal function in an animal or human subject using renal scintigraphy, comprising: (a) administering to an animal or human subject an amount of a renal tracer, where the renal tracer comprises a metal tricarbonyl complex disclosed herein or mixtures; (b) obtaining at least one image of a kidney of the animal or human subject, wherein the image is obtained as a data output from a gamma camera; and (c) analyzing the data output from the gamma camera, wherein the data analysis provides a measurement of the effective renal plasma flow of the animal or human subject.

In certain embodiments of the disclosure, the methods may further comprise repeating the steps (a)-(c), thereby providing a time-dependent analysis of the urinary tract function of an animal or human subject, wherein the analysis is selected from the group consisting of: the EPRF of a kidney, the ability of a kidney to extract the tracer from the blood, the ability of subject human or animal to excrete the tracer into the collecting system of a kidney, monitoring of drainage of the tracer from the collecting system (calyces and pelvis) to the bladder, and to quantify the ability of the bladder to empty.

In other embodiments of the disclosure, the methods may further comprise repeating the steps (a)-(c) at least once, thereby providing a series of images and a time-dependent analysis of renal efficiency of the animal or human subject.

In another embodiment of the disclosure, the methods may further comprise repeating the steps (b) and (c) after a single amount of the renal tracer obtaining a series of images of the kidney or kidneys of the animal or human subject, and analyzing the data output from the gamma camera, wherein the data analysis provides a measurement of the effective renal plasma flow of the animal or human subject.

In one embodiment of this aspect of the disclosure, the steps (a)-(c) may be repeated at time intervals over a period of about 2 mins to 60 mins, thereby providing a time-dependent series of images.

In another embodiment, the steps (a)-(c) are repeated at time intervals over a period of about 3 mins to 30 mins, thereby providing a time-dependent series of images.

In certain embodiments, the disclosure contemplates method of measuring effective renal plasma flow in an animal or human subject, comprising administering to an animal or human subject an amount of a renal tracer, wherein the renal tracer comprises a metal tricarbonyl complex disclosed herein or mixtures, isolating a series of biological samples from the animal or human subject after administering the renal tracer, quantitatively detecting the amount of the renal tracer in the biological samples, and determining the effective renal plasma flow of the animal or human subject.

In certain embodiments, the disclosure relates to imaging methods comprising a) administering a metal tricarbonyl complex comprising a radionuclide or positron-emitting radionuclide disclosed herein or mixtures to a subject; and b) scanning the subject for the emission, positron-emissions or other gamma-emissions.

The methods typically further comprise the steps of detecting the emissions and creating an image of an area of the subject indicating or highlighting the location of the metal tricarbonyl complex containing radionuclide or mixtures in the subject. In certain embodiments, the area of the subject is the lymph nodes, groin, axilla, neck, lungs, liver, kidney, pancreas, stomach, balder, intestines, circulatory system, breast, prostate, gallbladder, or brain.

The metal tricarbonyl complexes of the present disclosure may be labeled with one or more radionuclides, such as $^{11}C$, or $^{18}F$, $^{76}Br$, $^{123}I$, $^{124}I$, $^{131}I$, $^{13}N$, or $^{15}O$. Radionuclides used in PET scanning are typically positron-emitting isotopes with short half-lives such as carbon-11 (approximately 20 min), nitrogen-13 (approximately 10 min), oxygen-15 (approximately 2 min), and fluorine-18 (approximately 110 min). The metal tricarbonyl complex may be administered by any suitable technique known in the art, such as direct injection. Injection may be intravenous (IV). Administration may be general or local to the site of interest. The compound may be used in conjunction with another probe. The two (or more) probes may be administered together, separately or sequentially. The metal tricarbonyl complexes of the present disclosure may be used to diagnose, assess or monitor the progression or treatment of a disease or condition.

The metal complexes of the disclosure are useful as tracer compounds for kidney functioning and blood circulating imaging techniques, including PET and SPECT imaging. Particularly useful as an imaging agent are those compounds labeled with F-18 since F-18 has a half-life of 110 minutes, which allows sufficient time for incorporation into a radio-labeled tracer, for purification and for administration into a human or animal subject. In addition, facilities more remote from a cyclotron, up to about a 200 mile, radius can make use of F-18 labeled compounds.

Other halogen isotopes can serve for PET or SPECT imaging, or for conventional tracer labeling. These include $^{75}Br$, $^{76}Br$, $^{77}Br$ and $^{82}Br$ as having usable half-lives and emission characteristics. In general, the chemical means exist to substitute any halogen moiety for the described isotopes. Astatine can be substituted for other halogen isotopes, [$^{210}At$] emits alpha particles with a half-life of 8.3 h. At-substituted compounds are therefore useful for tumor therapy where binding is sufficiently tumor-specific.

In certain embodiments, the disclosure provides methods for kidney imaging using PET and SPECT. The methods entail administering to a subject (which can be human or animal, for experimental and/or diagnostic purposes) an image-generating amount of a metal tricarbonyl complex of the disclosure or mixtures, labeled with the appropriate isotope and then measuring the distribution of the metal tricarbonyl complex by PET if [$^{18}F$] or other positron emitter is employed, or SPECT if [$^{99m}Tc$] or other gamma emitter is employed. An image-generating amount is that amount which is at least able to provide an image in a PET or SPECT scanner, taking into account the detection sensitivity and noise level of the scanner, the age of the isotope, the body size of the subject and route of administration.

It will be understood that compounds of the disclosure can be labeled with an isotope of any atom or combination of atoms in the structure. While [$^{18}F$], [$^{99m}Tc$] and have been emphasized herein as being particularly useful for PET, SPECT and tracer analysis, other uses are contemplated including those flowing from physiological or pharmacological properties of stable isotope homologs and will be apparent to those skilled in the art.

Methods of use of the imaging agents provided herein include, but are not limited to: methods of imaging kidney tissue; methods of imaging kidney function; methods of diagnosing kidney function; methods of monitoring the progress of kidney issue degeneration; methods of imaging abnormal kidney tissue, and the like. The methods can be used to detect, study, monitor, evaluate, and/or screen, biological events in vivo or in vitro.

In diagnosing and/or monitoring pharmaceutical compositions comprising the metal tricarbonyl complexes disclosed herein or mixtures are administered to the subject in an amount effective to result in uptake of the complex into the blood stream. After administration of the complexes, the complexes are detected using PET or SPECT imaging. Embodiments of the present disclosure can non-invasively image the presence of the complexes in the blood and tissue throughout an animal or patient.

In preferred methods of the present disclosure, the metal tricarbonyl complexes of the present disclosure are excreted from tissues of the body quickly to prevent prolonged exposure to the radiation of the radiolabeled complexes administered to the patient. In particular embodiment, the radionuclide labeled complexes provided herein can be used on an outpatient basis. Typically metal complexes of the present disclosure are eliminated from the body in less than about 24 hours. More preferably, complexes of the present disclosure are eliminated from the body in less than about 16 hours, 12 hours, 8 hours, 6 hours, 4 hours, 2 hours, 90 minutes, or 60 minutes.

The spatial distribution of the complexed disclosed herein may be measured using any imaging apparatus suitable for the particular label, for example, a gamma camera, a PET apparatus, a SPECT apparatus, MRS, MRI or optical imaging apparatus, and the like. The extent of accumulation of the imaging agent may be quantified using known methods for quantifying radioactive emissions. A particularly useful imaging approach employs more than one imaging agent to perform simultaneous studies. Alternatively, the imaging method may be carried out a plurality of times with increasing administered dose of the pharmaceutically acceptable imaging composition of the present disclosure to perform successive studies using the split-dose image subtraction method, as are known to those of skill in the art.

Preferably, an amount of the imaging agent effective for imaging kidney function is administered to a subject. An effective amount of the imaging agent may be administered in more than one injection. The effective amount of the imaging agent can vary according to factors such as the degree of susceptibility of the individual, the age, sex, and weight of the individual, idiosyncratic responses of the individual, the dosimetry, and the like. Effective amounts of the imaging agent can also vary according to instrument and film-related factors.

EXAMPLES

Evaluation of $^{99m}$Tc(CO)$_3$(FEDA): A Dual-Purpose $^{99m}$Tc/$^{18}$F Renal Imaging Agent N-(2-fluoroethyl)iminodiacetic acid (FEDA) was prepared by the reaction of 1-bromo-2-fluoroethane with dimethyl 2,2'-iminodiacetate, followed by an alkaline hydrolysis of methyl esters. FEDA was labeled using an IsoLink kit and purified by HPLC. $^{99m}$Tc-tricarbonyl ([$^{99m}$Tc(CO)$_3$]$^+$) is produced in the form of its aqua ion [$^{99m}$Tc(CO)$_3$(H$_2$O)]$^+$ in a one-step reaction by reduction of the generator-eluted form of $^{99m}$Tc, sodium pertechnetate ([$^{99m}$TcO$_4$]$^-$). See Waibel et al. Nat Biotechnol 1999, 17: 897-901.

$^{99m}$Tc(CO)$^3$(FEDA) was evaluated in rats using $^{131}$I-OIH as an internal control; urine was analyzed for metabolites. Plasma protein binding (PPB) and erythrocyte uptake (RCB) were determined from the 10 min blood samples. The Re(CO)$_3$ analog was prepared for structural characterization.

Figure 1:
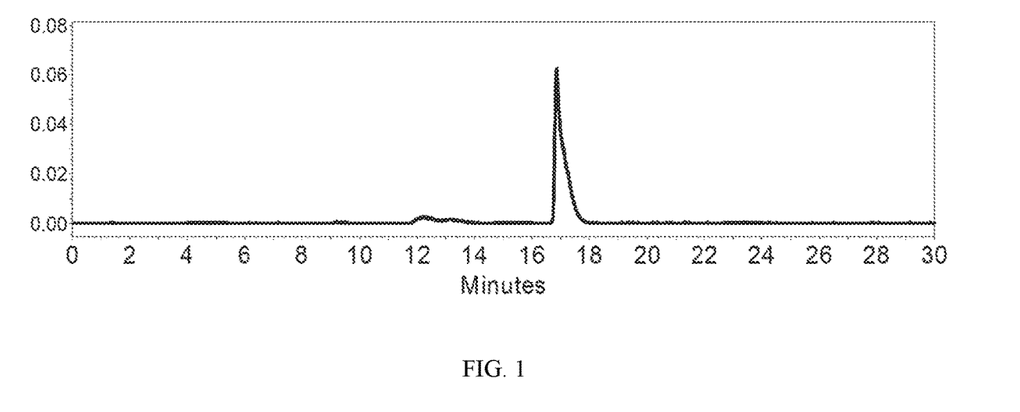
FIG. 1 shows the HPLC chromatograms of $^{99m}$Tc(CO)$_3$ (FEDA) in urine at 10 min after injection.

$^{99m}$Tc(CO)$_3$(FEDA) was efficiently prepared as a single species with high radiochemical purity (>99%), and was stable through 24 h at physiological pH. It showed rapid blood clearance, high specificity for renal excretion and lack of significant uptake in other organs. The % injected dose in the urine was 100% and 99% that of $^{131}$I-OIH at 10 and 60 min, respectively. The tracer was secreted intact in the urine; PPB was 61% and RCB was 20%.

Dimethyl N-(2-Fluoroethyl)Iminodiacetate (1)

Dimethyl iminodiacetate hydrochloride (1 g, 5.0 mmol) and 1-bromo-2-fluoroethane (0.63 g, 5.0 mmol) were combined with 5 mL MeCN and diisopropylamine (1.2 mL, 11 mmol) in an oven-dried 10 mL sealed tube. The tube was heated in an oil bath at 90° C. for 3 d. The reaction mixture was concentrated, and the crude yellow solid was purified by flash chromatography (97% CHCl$_3$, 3% MeOH; 10 mL fractions). Fractions 6-20 yielded the product as a slightly yellow oil (0.77 g, 3.7 mmol, 74%), sufficiently pure for subsequent reactions. $^1$H NMR (400 MHz, CDCl$_3$) δ: 4.58 (doublet of triplets, 2H, J$_{FE}$=48 Hz, J$_{HH}$=5.6 Hz), 3.71 (s, 6H), 3.64 (s, 4H), 3.10 (doublet of triplets, 2H, J$_{F-H}$=28 Hz, J$_{H-H}$=5.6 Hz). $^{19}$F NMR (400 MHz, CDCl$_3$, TFA reference) δ: 222.41 ppm. HRMS (M$^+$, ESI) Calc'd for C$_8$H$_{14}$O$_4$NFNa: 230.07991, found: 230.07986 (Δ=−0.05 mmu, −0.21 ppm).

N-(2-Fluoroethyl)Iminodiacetic Acid (2, FEDA)

Compound 1 (0.12 g, 0.5 mmol) was dissolved in 4 mL methanol before the addition of 2M NaOH (2 mL). The solution was stirred at room temperature for 24 h, neutralized with 1M HCl. The reaction mixture was evaporated and the crude product was desalted on a Sephadex G-15 column, into 3 min fractions. A TLC plate was spotted with each fraction and those containing the product were identified by a basic permanganate stain. Appropriate fractions were concentrated to yield 2 as a colorless oil (76 mg, 0.42 mmol, 84%). $^1$H NMR (400 MHz, D$_2$O, pH9) δ: 4.58 (doublet of triplets, 2H, J$_{FH}$=48 Hz, J$_{HH}$=4.8 Hz), 3.33 (s, 4H), 3.01 (doublet of triplets, 2H, J$_{F-H}$=28 Hz, J$_{H-H}$=4.8 Hz). $^{19}$F NMR (400 MHz, CDCl$_3$, TFA reference) δ: 221.2 ppm. HRMS (M$^+$, ESI) Calc'd for C$_6$H$_{10}$O$_4$NFNa: 202.04970, found: 202.04906 (Δ=−0.64 mmu, −3.19 ppm).

Re(CO)$_3$(FEDA) (3)

An aqueous solution of 2 (25 mg, 0.12 mmol) was combined with a stirred solution of 0.1 M [Re(CO)$_3$(H$_2$O)$_3$]OTf (0.12 mL, 0.12 mmol). The pH of the reaction mixture was immediately adjusted to 6 using 1 M NaOH and monitored by HPLC. A small aliquot was heated at 70° C. for 5 min and examined by HPLC; the reaction was complete. The remainder of the reaction proceeded to completion within 90 min at room temperature. HPLC analysis revealed the major product peak with a retention time of 16.5 min. The reaction mixture was concentrated to 1 mL and purified over Sephadex G-15 gel. UV active fractions were analyzed by HPLC and combined to yield the product in >90% purity by HPLC. %). $^1$H NMR (400 MHz, D$_2$O, pH 7) δ: 4.75 (doublet of triplets, 2H, J$_{FH}$=48 Hz, J$_{HH}$=4.8 Hz), 3.94 (d, 2H, J=16.4 Hz), 3.79 (doublet of triplets, 2H, J$_{F-H}$=28 Hz, J$_{H-H}$=4.8 Hz), 3.73 (d, 2H, J=16.4 Hz). $^{19}$F NMR (400 MHz, CDCl$_3$, TFA reference) δ: 217.61 ppm. HRMS (M$^-$, ESI) Calc'd for C$_9$H$_8$O$_7$NF$^{187}$Re: 447.98478, found: 447.98438 (Δ=−0.40 mmu, −0.89 ppm).

Re(CO)$_3$(HDA-Ts) (4)

Re(CO)$_3$(HDA), prepared from 2-hydroxyethyl iminodiacetic acid and Re(CO)$_3$(H$_2$O)$_3$[OTf], was dissolved in THF and stirred in an oil bath at room temperature with p-toluenesulfonyl chloride (29 mg, 0.15 mmol), triethylamine (21 μL, 0.15 mmol) and a catalytic amount of dimethylaminopyridine (3 mg) overnight. The starting material was consumed, giving rise to a single product peak with a retention time of 23 min. The crude product was purified over silica using a water:isopropanol:ethylacetate (7:2:1) mobile phase. UV active fractions were combined and concentrated to yield the product 4 as a white powder (10 mg, 0.02 mmol, 20%).

$^{18}$F—Re(CO)$_3$(FEDA) (3) from $^{18}$F-Labeling Precursor, (4)

Re(CO)$_3$($^{18}$FFEDA) (3) was prepared by reacting the corresponding tosyl precursor, rheniumtricarbonyl-N-ethyltosylate iminodiacetate, Re(CO)$_3$(TsDA), with [18F]fluoride ion ($^{18}$F) in anhydrous acetonitrile in the presence of K$_2$CO$_3$ and Kryptofix 222 at 110° C. for 20 min in a chemical processing control unit (CPCU). The resulting radiolabeled product was purified by semi-preparative high performance liquid chromatography (HPLC) using a Waters XTerra Prep RP 18 column (5 μm, 19×100 mm) and eluted with a mobile phase of 0.05 M triethylammonium phosphate (TEAP) buffer (pH=7)/ethanol (80:20 v/v) at a flow rate of 6 mL/min. The solution of the $^{18}$F radiotracer (pH 7) was analyzed by HPLC for stability for up to 23 h.

Re(CO)$_3$($^{18}$FFEDA) was obtained by the nucleophilic substitution fluorination in the decay corrected radiochemical yield of 18% in a total synthesis time of 120 min from end of bombardment. The purified filtered final radiotracer was formulated in a 0.05 M TEAP solution containing 10% ethanol. Quality control showed radiochemical and chemical purities above 99%. Coinjection with the standard Re(CO)$_3$(FEDA) confirmed the identity of the radiolabeled product. The HPLC analysis of an aliquot of Re(CO)$_3$($^{18}$FFEDA) incubated for 23 hours revealed only intact $^{18}$F radiotracer confirming its stability.

$^{99m}$Tc(CO)$_3$(FEDA) (5)

The ligand 2 was heated with the labeling precursor [$^{99m}$Tc(CO)$_3$(H$_2$O)$_3$]OTf for 30 min before purifying by HPLC. Coinjection with the cold standard showed the product 5 was isolated in high purity. The tracer 5 was stable under physiological conditions for at least 1 d and used in animal studies.

The invention claimed is:

1. A metal tricarbonyl complex comprising a N-(2-fluoroethyl) iminodiacetate ligand or $^{18}$F analog thereof and a metal tricarbonyl.

2. The metal tricarbonyl complex of claim 1 having the formula Re(CO)$_3$(N-(2-$^{18}$fluoroethyl)iminodiacetate).

3. The metal tricarbonyl complex of claim 1 having the formula $^{99m}$Tc(CO)$_3$(N-(2-fluoroethyl)iminodiacetate).

4. A composition comprising a mixture of Re(CO)$_3$(N-(2-$^{18}$fluoroethyl)iminodiacetate) and $^{99m}$Tc(CO)$_3$(N-(2-fluoroethyl)iminodiacetate).

5. A metal tricarbonyl complex Re(CO)$_3$(N-(2-((tosyl)oxy)ethyl)iminodiacetate.

* * * * *